US010951837B2

(12) United States Patent
Alzaga et al.

(10) Patent No.: US 10,951,837 B2
(45) Date of Patent: Mar. 16, 2021

(54) GENERATING A STEREOSCOPIC REPRESENTATION

(71) Applicant: Siemens Healthcare GmbH, Erlangen (DE)

(72) Inventors: Amilcar Alzaga, Nuremberg (DE); Alois Regensburger, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/523,998

(22) Filed: Jul. 26, 2019

(65) Prior Publication Data
US 2020/0036910 A1     Jan. 30, 2020

(30) Foreign Application Priority Data
Jul. 27, 2018    (EP) .................................... 18186096

(51) Int. Cl.
*H04N 5/272*      (2006.01)
*G06T 7/33*       (2017.01)
(Continued)

(52) U.S. Cl.
CPC ............. *H04N 5/272* (2013.01); *G06T 7/33* (2017.01); *G06T 7/70* (2017.01); *G06T 17/00* (2013.01);
(Continued)

(58) Field of Classification Search
None
See application file for complete search history.

(56) References Cited

U.S. PATENT DOCUMENTS

2010/0094124 A1*   4/2010   Schoonenberg .......... G06T 7/33
                                                  600/424
2013/0218024 A1*   8/2013   Boctor ................. A61B 8/0841
                                                  600/476
(Continued)

FOREIGN PATENT DOCUMENTS

WO      WO2015023990 A1     2/2015

OTHER PUBLICATIONS

European Search Report for European Patent Application No. 18186096.6-1124 dated Sep. 13, 2019.
(Continued)

*Primary Examiner* — Ryan M Gray
(74) *Attorney, Agent, or Firm* — Lempia Summerfield Katz LLC

(57) ABSTRACT

A camera image is acquired by a camera and a structure that is optically concealed in the camera image is acquired by a material-penetrating acquisition modality. A stereoscopic depth location of a common reference point is then fixed at a predetermined value. The stereoscopic representation is then generated from the camera image, and an overlay image is generated based on the concealed structure. In this case, a depth location of the camera image is fixed at the depth location of the reference point, and, as a function thereof, a depth location of the overlay image is adjusted in relation to the depth location of the reference point, such that in the stereoscopic representation, the overlay image appears realistically in front of and/or behind an optically opaque part in the recording direction of the camera image.

17 Claims, 2 Drawing Sheets

(51) Int. Cl.
G06T 7/70 (2017.01)
H04N 13/128 (2018.01)
H04N 13/156 (2018.01)
G06T 17/00 (2006.01)

(52) U.S. Cl.
CPC ......... *H04N 13/128* (2018.05); *H04N 13/156* (2018.05); *G06T 2207/10088* (2013.01); *G06T 2207/10116* (2013.01); *G06T 2207/20212* (2013.01); *G06T 2207/30004* (2013.01); *G06T 2207/30108* (2013.01); *G06T 2207/30204* (2013.01)

(56) References Cited

U.S. PATENT DOCUMENTS

| | | | | |
|---|---|---|---|---|
| 2013/0245461 | A1* | 9/2013 | Maier-Hein | A61B 5/742 600/476 |
| 2018/0308247 | A1* | 10/2018 | Gupta | G01N 23/046 |
| 2019/0247132 | A1* | 8/2019 | Harks | A61B 8/5284 |

OTHER PUBLICATIONS

Kutter, Oliver, et al. "Real-time volume rendering for high quality visualization in augmented reality." International Workshop on Augmented environments for Medical Imaging including Augmented Reality in Computer-aided Surgery (AMI-ARCS 2008), New York, USA. 2008. pp. 1-10.

Bichlmeier, Christoph, and Nassir Navab. "Virtual window for improved depth perception in medical AR." International Workshop on Augmented Reality environments for Medical Imaging and Computer-aided Surgery (AMI-ARCS). 2006. pp. 1-5.

Bichlmeier, Christoph, et al. "Improving depth perception in medical ar." Bildverarbeitung für die Medizin 2007. Springer, Berlin, Heidelberg, 2007. 217-221.

SAGES Society of American Gastrointestinal and Endoscopic Surgeons: "Pre-clinical evaluation of a novel 2D to 3D conversion system using a standard 2D endoscope", (https://www.sages.org/meetings/annual-meeting/abstracts-archive/pre-clinical-evaluation-of-a-novel-2d-to-3d-conversion-system-using-a-standard-2d-endoscope/), May 24, 2018. pp. 1-3.

SAGES Society of American Gastrointestinal and Endoscopic Surgeons: "Real-time 2d-3d Image Converting Software With a Monocular Small Camera Toward the Lesser Invasive Laparoscopic Surgery", (https://www.sages.org/meetings/annual-meeting/abstracts-archive/real-time-2d-3d-image-converting-software-with-a-monocular-small-camera-toward-the-lesser-invasive-laparoscopic-surgery/), May 24, 2018. pp. 1-2.

Wikipedia: 2D to 3D conversion (https://en.wikipedia.org/wiki/2D_to_3D_conversion), Last edited Apr. 2018. pp. 1-5.

* cited by examiner

GENERATING A STEREOSCOPIC REPRESENTATION

This application claims the benefit of EP 18186096.6, filed on Jul. 27, 2018, which is hereby incorporated by reference in its entirety.

BACKGROUND

The present embodiments relate to generating a stereoscopic representation of a target object.

All manner of objects are examined and/or manipulated for all variety of purposes in many different application fields. The respective objects are often depicted by a camera in this case, and a corresponding camera image of the object is represented on a display device. This may be advantageous if, for example, an examination region of the object cannot easily be accessed or viewed (e.g., due to limited spatial conditions and/or lighting conditions that are inadequate for direct observation). Even in such situations, the currently available camera technology allows advantageously useful images to be generated. In restricted spatial conditions, a miniaturized endoscopic camera, for example, may be used. It is therefore possible to depict, for example, machine installations or industrial products as well as, for example, parts of building structures or infrastructure facilities, but also, for example, natural objects such as plants, animals, and humans or biological tissue samples.

When using an optical camera, the problem arises in this case that many materials are optically opaque, and therefore, regions that are arranged behind such an opaque material in the viewing direction of the camera cannot be depicted or at least cannot be depicted without the material being destroyed or damaged locally by the camera. If, for example, an X-ray device is used instead of the camera, it is then possible to penetrate optically opaque materials, but corresponding X-ray images are often less clear for a respective user and/or less detailed or less revealing due to the inherent characteristics of X-ray technology. With X-ray technology, materials that are at least substantially transparent for the X-radiation are not depicted. A further significant problem is that often only 2D camera images are recorded or available, and therefore, even if supporting arrows, subsidiary lines, contour lines, or similar are superimposed, no defined or reliable depth information or depth effect is present in corresponding representations. As a result of this, precise orientation and examination of the respective object is often significantly hampered.

SUMMARY AND DESCRIPTION

The scope of the present invention is defined solely by the appended claims and is not affected to any degree by the statements within this summary.

The present embodiments may obviate one or more of the drawbacks or limitations in the related art. For example, improved depiction of a target object that is at least partially optically opaque is provided.

An imaging system according to one or more of the present embodiments is used (e.g., configured) to generate a stereoscopic representation of a target object and has at least an acquisition device and a data processing device (e.g., a data processor) for this purpose. The acquisition device is configured to acquire an optical camera image of an optically opaque part of the target object. The acquisition device is further configured to acquire, by a material-penetrating acquisition modality, a structure that is optically concealed by the opaque part (e.g., arranged behind the opaque part) in a recording direction of the camera image. The acquisition device may therefore include, for example, a camera for recording the camera image. The acquisition device may further include, for example, an X-ray or MRT device as the material-penetrating acquisition modality. However, the material-penetrating acquisition modality may additionally or alternatively include a tracking device likewise (e.g., for electromagnetic tracking). In this case, the acquisition of the structure may signify or include an acquisition and/or tracking of a position and location (e.g., pose) of the structure, for which purpose the structure may have, for example, a corresponding marker (e.g., an electromagnetic transmit coil). In the context of the present embodiments, the acquisition may likewise signify that corresponding image data and/or acquisition data (e.g., data representing the camera image and/or the acquired structure) is retrieved by the acquisition device from a data store or a corresponding data source that is provided.

The optically opaque part of the target object may be, for example, a wall or wall part or a surface of the target object. Depending on the type of target object, this may be, for example, a housing wall or intermediate wall, a tissue wall, an outer side, an organ surface, etc. The optically concealed structure may be an internal part of the target object itself, but may likewise be or include, for example, a foreign object that is arranged in or at the target object (e.g., a foreign body, an instrument, a tool, or similar).

The data processing device of the imaging system of one or more of the present embodiments is configured to automatically specify a common reference point that is depicted in the camera image and by the material-penetrating acquisition modality. This reference point may therefore be ultimately any type of point that is both depicted and recognizable in the camera image and is identifiable in the acquisition data acquired or generated or provided by the material-penetrating acquisition modality. For example, the reference point may be specified automatically by an algorithm for object recognition and/or image processing. In addition, provision may also be made for the camera image to be registered with the acquisition data of the material-penetrating acquisition modality, and known methods may be used for this purpose. Following the registration, it is then possible to specify a common point (e.g., a contact point of respective acquired regions of the target object) as the reference point.

The data processing device is further configured to automatically fix a stereoscopic depth location (e.g., a vergence or parallax) of the reference point at a predetermined value. A vergence of 0 may be predetermined, for example, such that the stereoscopic depth location of the reference point in the ultimately generated stereoscopic representation lies in a plane of the screen or display. It is likewise possible to predetermine, for example, a specific virtual separation of the reference point from the plane of the screen or display in the ultimately generated stereoscopic representation (e.g., the distance which the reference point will appear to be from the plane of the screen or display). The reference point may be part of the opaque part of the target object, and therefore, lies on or in the surface thereof as depicted by the camera image.

The data processing device is further configured to automatically or semiautomatically generate or acquire an overlay image based on the acquired concealed structure. In the simplest case, this overlay image may be an image of the structure as acquired or generated by the material-penetrating acquisition modality. The overlay image may likewise be generated from the acquisition data of the material-penetrating acquisition modality by rotation, displacement, and/or distortion, for example, in order to adapt a representation or perspective of the overlay image to the recording direction (e.g., a perspective of the camera image). The overlay image may likewise be or include (e.g., represent) a model of the structure as generated from the acquisition data and/or at least a virtual object. The virtual object or the virtual representation may be or include, for example, a marking of a spatial region or an area, a subsidiary line, or similar. The at least one virtual object and/or the generated model may be two-dimensional (2D) or, for example, three-dimensional (3D).

The data processing device is further configured to automatically generate the stereoscopic representation from the camera image and the overlay image and in this case to automatically fix a stereoscopic depth location of the camera image at the stereoscopic depth location of the reference point. The data processing device is further configured to, as a function thereof, adjust a stereoscopic depth location of the overlay image in relation to the stereoscopic depth location of the reference point, such that in the stereoscopic representation, the overlay image, at least in or at the reference point, appears in front of and/or behind the optically opaque part in the recording direction of the camera image in accordance with a corresponding real location in front of and/or behind the optically opaque part. If the overlay image is or includes a model of the concealed structure, this model is therefore represented behind the optical opaque part in the stereoscopic representation, accordingly. If, however, the overlay image includes a virtual object, for which a real physical equivalent is not necessarily present, this object may be represented in front of and/or behind the optically opaque part, according to whether an equivalent or representation of the virtual object would be arranged in front of and/or behind the optically opaque part if translated into reality. It is, however, intended in this case that these location or depth relationships are valid at the reference point. At other points or in other regions of the stereoscopic representation, inconsistencies of the depth location are acceptable in the stereoscopic representation. This may apply or occur, for example, if the optically opaque part is depicted in two dimensions by the camera image but is spatially curved or bowed in reality.

The depth locations of the camera image and the overlay image or depth relationships of the camera image and the overlay image in the stereoscopic representation therefore relate explicitly to the reference point. At the reference point, the depth locations or depth relationships therefore correspond to the corresponding real spatial ratios. However, this is not necessarily the case at other points or in other spatial regions. The depth relationships (e.g., the relative stereoscopic depth locations) may be correct at other points or in other regions away from the reference point (e.g., correspond to the corresponding real spatial ratios) in terms of a respective depth location in front of and/or behind the optically opaque part. However, it is not necessary, for example, for absolute separations or distances or absolute distance ratios in a depth direction to correspond to the corresponding real absolute separations or distances or absolute distance ratios. It is therefore possible to dispense with corresponding spatial measurements, these being associated with considerable expense, and nonetheless give an observer an improved spatial impression of depth in comparison with a non-stereoscopic overlay.

Since the reference point is for the observer the only relevant connection between the optically opaque part (e.g., the visible surface depicted in or by the camera image) and the concealed structure lying behind the optically opaque part or the corresponding virtual structure, it is sufficient for the depth relationship to be applicable and correct at the reference point (e.g., to correspond to the real spatial ratios there).

If the overlay image is a model of the optically concealed structure, for example, this is then represented behind the reference point in the stereoscopic representation, in the predetermined observation direction thereof (e.g., at least virtually or stereoscopically further distant from the plane of the screen or display, with a smaller parallax, than the reference point and the camera image or image parts or image regions belonging to or originating from the camera image). Provision may then be made for not superimposing (e.g., not representing in the stereoscopic representation) any virtual structures that are situated closer than the stereoscopic depth location of the optically recorded camera image.

If, however, the camera image includes a virtual subsidiary line, for example, this may extend in a depth direction in the stereoscopic representation (e.g., from an image foreground into an image background). This subsidiary line (e.g., the overlay image) starting, for example, from a point or spatial region in front of the reference point in the stereoscopic representation may then pass through the opaque part and continue behind the opaque part. The fact that the overlay image is generated based on the optically concealed structure may then signify, for example, that the subsidiary line leads to the structure (e.g., ending at the structure or going past the structure with a predetermined minimum separation in order to define a safety zone and avoid any damage to the structure). The overlay image therefore depicts the structure itself and/or has a specific and, for example, predetermined spatial relationship to the structure in terms of location. Therefore, the overlay image may be a 3D image or a 3D data set. The acquisition data that is generated or acquired by the material-penetrating acquisition or imaging modality may likewise be a 3D image or a 3D data set.

The generated stereoscopic representation is therefore a composite stereoscopic image with a depth effect and combines the camera image with the overlay image (e.g., a superimposition). The optical camera image alone does not in itself provide any information about the concealed structure (e.g., a spatial region that lies out of sight of the camera behind the opaque part of the target object). An X-ray image recorded from, for example, a lateral direction may allow a rudimentary orientation in this spatial region that is not depicted by the camera or the camera image. For the purpose of precise orientation (e.g., for controlling an instrument or tool in this spatial region), this is, however, not optimal because such differing viewing representations (e.g., a camera image and an X-ray image) and refocusing on a respective display device require a user or observer to have particularly good spatial imagination skills as well as mental adjustment times. Known methods involve, for example, a superimposition of 2D information such as, for example, arrows or contour lines on the monoscopic camera image, but no depth information is thereby supplied or communicated in a view of this 2D camera image; therefore, precise orientation or navigation is barely possible.

By comparison, one or more of the present embodiments have the advantage that all of the relevant items of information or data are combined in a single image (e.g., the stereoscopic representation), and in this way, are meaningfully and realistically related with respect to depth location.

A particular difficulty may arise if the optically opaque part of the target object depicted by the camera image is itself curved (e.g., exhibits an elongation in the viewing direction or recording direction of the camera image (in the stereoscopic depth direction)). This opaque part is nevertheless represented as being flat in the 2D camera image. If the overlay image (e.g., a virtual 3D structure or 3D superimposition that is spatially elongated in a depth direction) is now simply overlaid or superimposed on the 2D camera image, the overlay image (e.g., the superimposed 3D structures) would have an unspecified depth location relationship to the 2D camera image (e.g., to the opaque part depicted thereby). For example, this unspecified depth relationship (e.g., spatial location relationship in a depth direction) may not be right (e.g., correct or realistic) everywhere in the resulting overall image or everywhere in the camera image (e.g., in all regions of the opaque part that is spatially elongated in the depth direction).

This difficulty is overcome by the present embodiments, in that the depth location of the camera image (e.g., of the depicted opaque part) is fixed at the depth location of the reference point, whereby a meaningful and consistent depth location relationship in the stereoscopic representation is enabled and achieved. Therefore, the depth location of the reference point is selected as an alignment point. Since the reference point is identifiable not only in the camera image but also in the acquisition data obtained by the material-penetrating acquisition modality, a depth location of this point in the acquisition data may be fixed at the same stereoscopic depth location (e.g., the same vergence or parallax), at which the reference point and the camera image are represented in the stereoscopic representation. The reference point therefore serves as a depth reference between the two different images or data sets (e.g., the camera image and the acquisition data of the material-penetrating acquisition modality). The present embodiments therefore allow an extended visualization, which allows particularly precise and efficient orientation and navigation by representing all of the available data items in combination, with a suitable and, for example, realistic depth location relationship to each other, in a single stereoscopic representation.

The imaging system of one or more of the present embodiments may also include a display device that is connected to the data processing device for the purpose of displaying the stereoscopic representation. This display device may therefore be a stereo display device (e.g., a 3D image screen or a suitable stereo data headset or similar).

A method according to one or more of the present embodiments is used to generate a stereoscopic representation of a target object by an imaging system (e.g., by the imaging system). In a method act of the method, an optical camera image of an optically opaque part of the target object is acquired by a corresponding acquisition device. In a further method act, a structure that is optically concealed by the opaque part in a recording direction of the optical camera image is acquired by a material-penetrating acquisition modality. This may be effected by a separate acquisition device or the same acquisition device as was used to acquire the optical camera image. In a further method act, a common reference point that is depicted in the camera image and by the material-penetrating acquisition modality (e.g., in corresponding acquisition data) is automatically specified by a correspondingly configured data processing device. In a further method act, a stereoscopic depth location of the reference point is automatically fixed at a predetermined value, likewise by the or a data processing device. In a further method act, an overlay image is automatically generated based on the acquired concealed structure, likewise by the or a data processing device. In a further method act, the stereoscopic representation of the target object is automatically generated from the optical camera image and the overlay image, likewise by the or a data processing device. In this case, a stereoscopic depth location of the optical camera image is automatically fixed at the set stereoscopic depth location of the reference point. As a function of this depth location, a stereoscopic depth location of the overlay image is adjusted in relation to the stereoscopic depth location of the reference point, such that in the resulting stereoscopic representation, the overlay image, at least at the reference point, appears (e.g., is superimposed or represented) in front of and/or behind the optically opaque part in a recording direction of the optical camera image in accordance with a corresponding real location in front of and/or behind the optically opaque part. In the resulting stereoscopic representation, the overlay image may therefore be represented as appearing in front of and/or behind the optically opaque part, at least at the reference point, corresponding to respective real ratios in a recording direction of the optical camera image. The real spatial ratios in this case specify how the opaque part and the concealed structure are spatially arranged relative to each other in reality and/or how an object represented as part of the overlay image would be arranged in reality (or translated into reality) in relation to (e.g., relative to) the opaque part and/or to the concealed structure. Reference is explicitly made to the corresponding explanations in connection with the imaging system of one or more of the present embodiments, which apply correspondingly to the method of one or more of the present embodiments.

The method of one or more of the present embodiments may therefore be an operating method for the imaging system, or regarded as such. A surgical step (e.g., for the purpose of positioning the camera and/or an instrument or tool that forms the structure or is provided for the purpose of manipulating the structure) may not be part of the method. Such a surgical step is not required for the purpose of performing or applying the method. Nonetheless, the method may be applied during or in parallel with an interventional action. In a medical application case, the method may likewise be applied to tissue samples or tissue parts outside the body of a human or animal, for example. The camera image may likewise be recorded entirely without intervention and from outside the body, for example, where the opaque part may then be a skin surface, for example. The structure that is optically concealed thereby may be a bone or an artificial metallic object, for example, which is acquired or depicted by an X-ray device as a material-penetrating acquisition modality. The camera image may be recorded by a capsule camera that may be swallowed and positioned without surgical intervention.

The method may also be used advantageously in other application fields beyond medicine or medical technology. For example, repairs or diagnostic examinations of machines or devices may be assisted by the method, with the advantage that the respective machine or device need not be dismantled, while precise and reliable spatial orientation and navigation are nonetheless possible in a respective internal region.

In an embodiment, a penetration point of an instrument or tool through the optically opaque part is specified as the reference point. The penetration point is therefore a point or region in which the instrument or tool reaches through the opaque part and therefore transits from a region that is depicted by the camera image into a region that is concealed by the opaque part. This penetration point may be referred to as an instrument entry point. If, for example, an X-ray or fluoroscopy device is used as the material-penetrating imaging or acquisition modality, this penetration point or instrument entry point may be recognized and identified in corresponding X-ray or fluoroscopy images as, for example, a transition point between air and a solid tissue material along the instrument. The use of this penetration point as the reference point is particularly advantageous since this may usually be identified particularly accurately and unambiguously (e.g., reliably), and may advantageously always be depicted by the camera in any case. Selecting the penetration point as a reference point advantageously allows a particularly accurate and reliable representation if, for example, the instrument or a model of the instrument is generated or superimposed as part of the overlay image. This is the case because the depth location of the reference point is specified unambiguously and is true to reality, such that even if the opaque part itself exhibits a spatial elongation depthwise, no optical discrepancies occur whatsoever, and a particularly precise association of the overlay image with the camera image is possible.

In a further embodiment, a 3D model of the optically concealed structure is generated as part of the overlay image. In a further embodiment, a travel path for a predetermined object is generated as part of the overlay image. The travel path may be, for example, a planned path along which the object is to be guided. Equally, the travel path may be a path that is acquired and tracked (e.g., a previous trajectory) of the predetermined object. The predetermined object may be an instrument or a tool, for example. However, the object may equally be a foreign body, or part of the target object itself that is to be transferred along the travel path to a predetermined destination position. The concealed structure may be part of the target object and/or the instrument or tool, for example. Because the 3D model of the structure is generated as a virtual object and used as part of the overlay image, the structure may advantageously be represented in the stereoscopic representation in a particularly precise and easily recognizable manner. The stereoscopic representation may therefore be recognized more easily overall, while orientation and navigation may be particularly precise and simple. As explained above, the travel path in this case may extend, for example, at least partially in the depth direction. This is possible for the first time in a reliable manner and in a manner that is unambiguously recognizable and is consistent with the representation of the camera image, as a result of the stereoscopic representation that is generated by the present embodiments.

In a further embodiment, a 2D position of the reference point is specified in an image plane of the camera image that is perpendicular to the recording direction of the camera image. In other words, X and Y coordinates of the reference point are therefore specified in the 2D camera image. This 2D position of the reference point in the camera image is then used for the 2D registration of the overlay image with the camera image in the corresponding image plane. In other words, the overlay image or the underlying acquisition data is therefore shifted in X and Y directions (e.g., perpendicularly relative to the depth direction), such that the reference point is situated at the same 2D position (e.g., has the same X and Y coordinates) in a corresponding common system of coordinates of the camera image and the acquisition data or the overlay image. Equally, the camera image may naturally be shifted likewise in a corresponding manner relative to the overlay image or the corresponding acquisition data. As a result of using the reference point not only as a depth reference but also as a reference for the 2D position, it is possible in a particularly simple and consistent manner to achieve a reliable registration and, therefore, a representation that is as far as possible free of errors and artifacts, of the stereoscopic representation since the reference point is or, by definition or specification, must be unambiguously identifiable in both data sets in any case.

In a further embodiment, a marker that may be detected optically by the material-penetrating acquisition modality (e.g., that may be acquired and depicted) is used to indicate the reference point. In other words, the marker (e.g., a corresponding marking object) is therefore arranged at the reference point or in a fixed positional relationship (e.g., a fixed spatial location relationship) relative to the marker (e.g., before the overlay image is generated or even before the corresponding acquisition data is acquired or recorded). Equally, it is possible first to position the marker and then to use the position of the marker, or a point having a predetermined fixed spatial location relationship with the position of the marker, as the reference point. This allows a particularly reliable and unambiguous specification of the location or position of the reference point in both the camera image and the acquisition data of the material-penetrating acquisition modality. The marker may be a metal clip, for example, or a known marker having X-ray visibility or X-ray opacity. The use of such a marker may be particularly advantageous if, for example, the opaque part depicted in the camera image has no reliably and unambiguously identifiable structures and/or is inherently movable or flexible. The use of the marker may be particularly advantageous if, for example, the instrument or tool has not yet been guided through the opaque part (e.g., no corresponding penetration point or instrument entry point yet exists) or if no instrument whatsoever is deployed. The latter may be the case, since the present embodiments may be used purely for the purpose of depiction.

In a further embodiment, part of the acquisition device that is used for recording the camera image (e.g., the camera or a head or endpiece of an endoscope in which the camera is arranged) is acquired by the material-penetrating acquisition modality (e.g., in the corresponding acquisition data). A location and viewing direction of this part of the acquisition device (e.g., in particular the camera) in relation to the reference point and/or in relation to the opaque part of the target object is then specified from the corresponding acquisition data. For example, an area or plane may therefore be defined in which the reference point is situated and which corresponds at least substantially to a corresponding surface of the opaque part or extends at least substantially along this surface or in the main extension plane thereof, and a vector may then be specified between the camera and the reference point or the defined plane. It is possible in this case to specify, for example, a separation between the camera and the reference point or a separation between the camera and the opaque part of the target object. Taking known inherent depiction properties of the camera into consideration, this allows a scaling or scale to be dimensioned or fixed for the camera image and structures depicted therein. In order to allow the location and viewing direction of the camera to be reliably and accurately specified in relation to the reference point or the opaque part, provision may be made, for example, for a depiction or acquisition direction in which the material-penetrating imaging or acquisition modality depicts or acquires the structure and the camera (e.g., the target object) to be arranged in a non-collinear manner relative to the recording direction of the camera image. The material-penetrating acquisition modality may therefore be arranged or aligned such that a corresponding region is depicted or acquired laterally (e.g., at least substantially perpendicular) to the recording direction of the camera.

Likewise, the depth location of the reference point for the stereoscopic representation may be fixed such that in this respect, a virtual or stereoscopic separation between the plane of the screen or display and the reference point corresponds to the actual real distance between the camera and that part or region of the opaque part of the target object that is used as a reference point. It is thereby possible to achieve a particularly realistic representation as well as a particularly accurate and specifically adapted positioning of the camera. Registration of the acquisition data with the camera image and consistent scaling or size representation of the overlay image are also made easier. This is not insignificant, because the material-penetrating acquisition modality may have fundamentally different depiction properties than the camera that is used to record the camera image.

In a further embodiment, in the stereoscopic representation, the camera image is automatically adapted in a region in which the camera image overlaps the overlay image, specifically by masking (e.g., virtual window), dimming, blurring, and/or partially transparent representation. In this manner, the impression of depth may be assisted (e.g., amplified or improved), and consequently, the stereoscopic depth relationship between the overlay image and the other regions of the camera image is easier to recognize. In this case, it is advantageous that the overlay image may extend beyond a boundary or field of view (e.g., a depiction region) of the camera image, where the corresponding superimposed structures or overlays are therefore at least partially represented outside the camera image. A depiction region or field of view of the stereoscopic representation may therefore also be extended beyond the field of view of the camera image. By this, the observer is provided with a larger context for better orientation and navigation. This is advantageous, since currently available endoscopic cameras may offer a relatively small field of view.

In a further embodiment, the camera image is recorded as a 2D image (e.g., monoscopically), and by fixing a stereoscopic depth location at the stereoscopic depth location of the reference point in the stereoscopic representation, the camera image is represented entirely and in an integrated manner at this stereoscopic depth location. In this embodiment variant, provision may be made for a 3D model or a 3D structure to be used as the overlay image to overlay the 2D camera image (e.g., combined with this to generate the stereoscopic representation). It is thereby possible at particularly little expense to generate an improved impression of depth for the observer and consequently simplify the task of orientation or navigation.

In a further embodiment, the camera image is recorded as a 2D image (e.g., monoscopically) and is converted by a 2D to 3D conversion method (e.g., possibly into a stereoscopic camera image) before the stereoscopic representation is generated. It is thereby already possible to achieve at least approximately a useful depth effect. The stereoscopic representation is then generated from the converted camera image and the overlay image, where for the purpose of fixing the stereoscopic depth location of the converted camera image, a partial region of the converted camera image containing the reference point is fixed at the stereoscopic depth location of the reference point. It is thereby possible to retain or maintain the defined depth location relationship between the reference point, the opaque part, and the overlay image, and at the same time, achieve a more realistic representation. For example, it is possible to make allowance for the fact that the opaque part of the target object may in reality have a spatial elongation in a depth direction, which may also be derived or unintentionally reconstructed at least partially from a 2D camera image by a human observer. By virtue of the conversion of the 2D camera image, a natural depth perception of the observer is advantageously assisted, thereby making it possible to further improve recognizability, orientation, and spatial navigation since possible perception conflicts may be avoided or minimized.

In a development, a 3D recording of the optically opaque part is recorded first, and a 3D model of the optically opaque part that is generated therefrom (e.g., automatically or semiautomatically) is then registered with the 2D camera image (e.g., automatically). The 3D model of the opaque part is then used as a basis or foundation or as a reference for the conversion of the 2D camera image. The 3D recording may correspond to the acquisition data that is recorded by the material-penetrating acquisition modality, in or by which the optically concealed structure and possibly the camera are also acquired or depicted. Equally, the 3D recording may be recorded separately during or in advance the method. The 3D recording may therefore be recorded, for example, already several days or even weeks before the camera image, and processed or prepared (e.g., segmented) in the meanwhile for the purpose of generating the 3D model. The 3D recording may be, for example, a 3D X-ray image, an MRT data set, or similar. While conventional methods for 2D to 3D conversion must rely on, for example, thrown shadows, contours, different degrees of sharpness, or similar, the presently described 3D recording and 3D model derived therefrom allows the 2D camera image to be converted in a manner that is closer to reality. Such a 3D recording of the corresponding region of the target object is often prepared in any case, and therefore, the corresponding data may be used efficiently in the manner described, incurring particularly little expense or load.

A further aspect is a computer program or computer program product (e.g., including a non-transitory computer-readable storage medium) that encodes or represents the method acts of at least one embodiment variant of the method and is configured to be loaded into a data store (e.g., a non-transitory data store) of an imaging system. The data store is electronic and/or electronically readable, for example, in order to execute the method acts (e.g., the method). The computer program may therefore include program means (e.g., instructions) for executing the method when the computer program is executed by the imaging system. For this purpose, the data store may be connected, for example, to a data processing device of the imaging system. The data processing device is configured to execute the computer program.

A further aspect is a data store or data medium (e.g., a non-transitory computer-readable storage medium) that is electronic and/or electronically readable, for example, in or on which is stored a computer program. For example, the data store may be a data store for a data processing device and/or a control device of the imaging system. In addition, further control instructions for the imaging system, the data processing device, and/or the control device may be stored or encoded in the data store (e.g., as part of the stored program code). The program code that is stored in the data store is therefore designed and configured, for example, to execute at least one variant of the method, or to cause the execution thereof, when the data store is used in the imaging system and the program code is executed by the imaging system, the data processing device, or the control device.

The imaging system may include, for example, such a data store. The imaging system (e.g., the data processing device thereof) may also have a processor device (e.g., a microprocessor and/or microcontroller) that is connected to the data store and is configured to execute the program code stored therein (e.g., to execute the computer program).

The imaging system cited in connection with the method, the computer program, and/or the data store may therefore be, for example, the imaging system, and correspondingly, vice versa. Accordingly, the imaging device, the computer program, and the data store may therefore have some or all of the properties and/or components cited in connection with the other aspects of the present embodiments (e.g., in connection with the method), and vice versa.

The properties and developments of the imaging system and the method specified above and in the following, and corresponding advantages, may each be analogically and reciprocally transferred between these and likewise to the other aspects of the present embodiments (e.g., to the computer program and the data store), and vice versa. Therefore, any developments of the imaging device, the method, the computer program, and the data store having embodiments that, in order to avoid unnecessary redundancy, are not described explicitly here in the respective combination or for each aspect of the present embodiments separately, likewise fall within the scope of the invention.

DETAILED DESCRIPTION

In the exemplary embodiments described below, the described components of the embodiment variants represent in each case individual features to be viewed independently of each other. The individual features also develop the present embodiments independently of each other in each case and are therefore to be considered as part of the present embodiments whether individually or in a combination other than that shown. The described embodiment variants may also be supplemented by further features described above.

Identical elements, functionally identical elements, or elements corresponding to each other are labeled by the same reference signs in each case in the figures.

Figure 1:
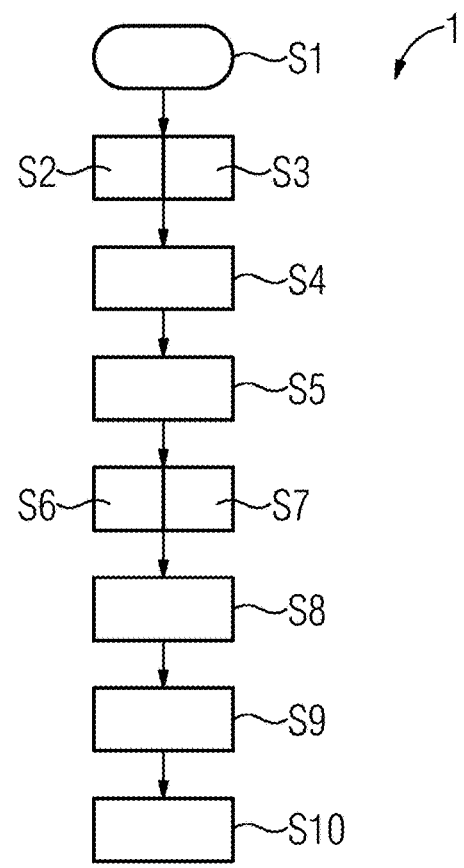
FIG. 1 shows an exemplary schematic flowchart of a method for generating a stereoscopic representation of a target object.
Figure 2:
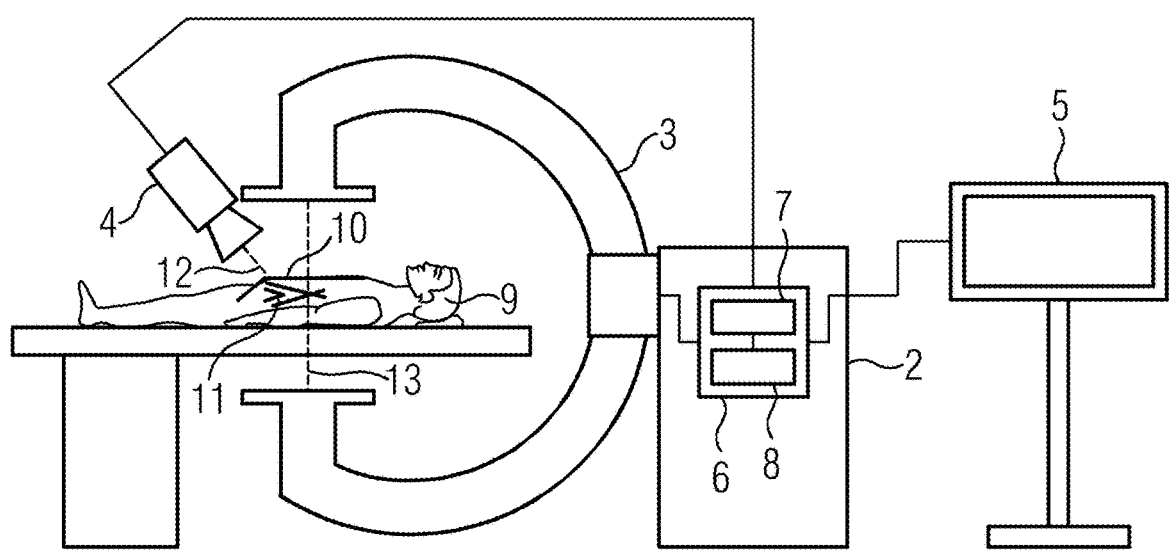
FIG. 2 shows a schematic representation of one embodiment of an imaging system for generating a stereoscopic representation of a target object.

FIG. 1 shows an exemplary schematic flowchart 1 of one embodiment of a method for generating a stereoscopic representation of a target object. This method is explained in greater detail with reference to the other figures. FIG. 2 shows a schematic representation of one embodiment of an imaging system 2 for generating the stereoscopic representation of the target object in accordance with the cited corresponding method.

The imaging system 2 in this case includes an X-ray device 3 as material-penetrating imaging or acquisition modality. The imaging system 2 also includes an optical camera 4. The embodiment variants of the X-ray device 3 and the camera 4 represented here are understood to be purely exemplary and schematic, and therefore, corresponding devices of different design may also be used. The imaging system 2 further includes a display device 5 that is intended to be a three-dimensional (3D) monitor in this case. The X-ray device 3, the camera 4, and the display device 5 are connected to a data processing device 6 of the imaging system 2 in this case. The data processing device 6 includes a processor device 7 (e.g., a processor) for processing camera images recorded by the camera 4 and acquisition data recorded by the X-ray device 3, and for outputting corresponding processing results (e.g., the stereoscopic representation that is to be generated in this case) to the display device 5. The data processing device 6 further includes a data store 8 that is connected to the processor device 7 and on which is stored a computer program that encodes the method acts of the cited method.

The method is started in a method act S1. The patient 9 as a target object may be positioned in a recording region of the X-ray device 3 and the camera 4, for example, and the imaging system 2 may be activated.

In a method act S2, an optical camera image of an optically opaque region 10 of the patient 9 is acquired by the camera 4. In a method act S3, which is, for example, concurrent therewith, an X-ray image of a concealed structure 11 of the patient 9 is recorded by the X-ray device 3. The concealed structure 11 is concealed in this case by the optically opaque region 10 from or in a recording direction 12 of the camera 4. The optically opaque region 10 is, however, at least partially transparent for the X-ray device 3, such that the X-ray image depicts the optically concealed structure 11. An acquisition direction 13 of the X-ray device 3 is not collinear to the recording direction 12 in this case (e.g., is aligned at an angle that differs from the recording direction 12 of the camera 4 by 0° to 180°). The camera image therefore has a different perspective than the X-ray image.

Figure 3:
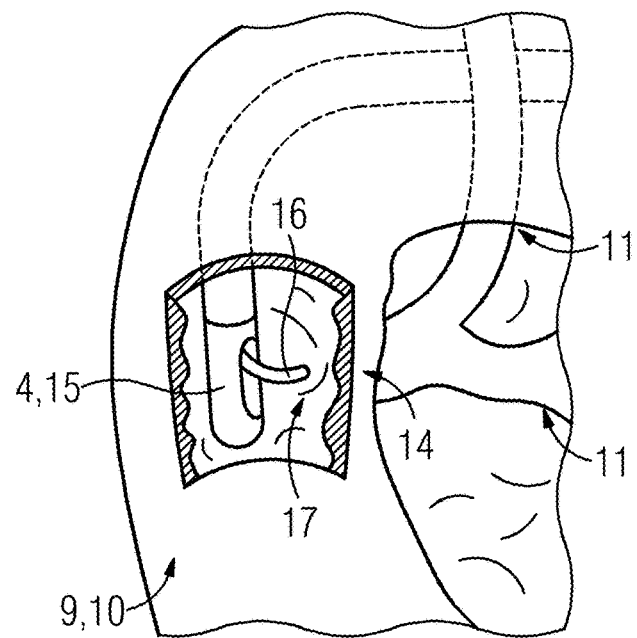
FIG. 3 shows a first schematic overview representation to illustrate the method.

FIG. 3 shows a schematic overview representation in order to illustrate such a situation. The opaque region 10 is, for example, formed by a tissue wall 14 of a vessel of the patient 9. An endoscope 15 is, for example, arranged in this vessel as a camera 4. A viewing or recording direction of the endoscope 15 is therefore directed at the optically opaque tissue wall 14, such that the concealed structure 11 that is situated spatially behind the tissue wall 14 may not therefore be depicted by the endoscope 15. An instrument 16 is arranged in the vessel together with the endoscope 15. The instrument 16 penetrates through the tissue wall 14 in the direction of the concealed structure 11.

In the case of an endoscopy of the gastrointestinal tract, for example, (e.g., in the case of endoscopic retrograde cholangiopancreatography (ERCP), optical camera images recorded by the flexible endoscope 15 often appear relatively identical). The endoscope 15 faces a wall of the stomach or intestine and only depicts the instrument 16 as far as an entry point at which the instrument 16 penetrates the wall (e.g., the tissue wall 14 in this case). The instrument 16 may be, for example, a cannula, a guide wire, a catheter, a needle, or similar. The optical camera image acquired by the endoscope 15 gives no information whatsoever about where the instrument 16 is arranged or moving in a region behind the tissue wall 14 and out of sight of the endoscope 15 in relation to the anatomy situated there (e.g., the concealed structure 11). Orientation in this region behind the tissue wall 14 is therefore usually only possible by a separate view of an X-ray or fluoroscopy image that is recorded, for example, perpendicular to the viewing or recording direction 12 of the endoscope 15. For example, a planned path may extend behind the tissue wall 14, along which the instrument 16 is to be guided to the concealed structure 11. The tissue wall 14 viewed by the endoscope 15 is typically not flat or even, but is spatially curved (e.g., exhibits a depthwise elongation in the recording direction 12).

In a method act S4, the camera image recorded by the camera 4 and the X-ray image recorded by the X-ray device 3 are processed by the data processing device 6. The data processing device 6 in this case specifies a common reference point 17 that is depicted (e.g., identifiable) in the camera image and in the X-ray image. In the example shown in FIG. 3, a penetration point at which the instrument 16 penetrates through the tissue wall 14 is specified as the reference point 17. In the case of an ERCP procedure, the reference point 17 may be an entry point of a cannula or other instrument 16 into the papilla as an entry point into the gall tract. In the case of laparoscopic ablation, the reference point 17 may be an entry point of an ablation needle into a corresponding organ surface. If no such penetration point is present in the respective application (e.g., because no instrument 16 is used), another point of the camera image may equally be used as the reference point 17 (e.g., a specifically distinctive structure of the opaque part 10). Therefore, 2D coordinates of the reference point 17 are specified in the camera image, and corresponding 3D coordinates of the reference point 17 are specified with reference to the X-ray or fluoroscopy image. For this purpose, it is likewise possible to use a plurality of X-ray or fluoroscopy images recorded from different acquisition directions 13.

In a method act S5, a stereoscopic depth location of the reference point 17 is fixed at a predetermined value. A vergence of 0 may generally be fixed for the reference point 17, for example, such that the reference point 17 will appear to be situated or superimposed on the surface of the screen in a corresponding stereoscopic representation. However, if the camera 4 is also depicted in the X-ray image, a separation from the reference point 17 or the tissue wall 14 on which the reference point 17 lies may be specified automatically and used as a basis for fixing the stereoscopic depth location of the reference point 17.

In an optional method act S6, the two-dimensional camera image is converted into a stereoscopic camera image by a corresponding 2D to 3D conversion method. Alternatively, the camera image is recorded as a 2D image and left as such. Concurrently therewith, for example, an overlay image is generated in a method act S7 based on the X-ray image and the optically concealed structure 11 depicted therein. In this case, the concealed structure 11 and a part of the instrument 16 that is situated behind the opaque part 10 and out of sight of the endoscope 15 or the camera 4 are virtually modeled in three dimensions. A spatial 3D travel path 23 (see FIG. 4) is also modeled.

In a method act S8, the camera image and the overlay image (e.g., the virtual 3D model that has been generated) are registered with each other (e.g., virtually arranged in a common system of coordinates corresponding to a spatial arrangement of their real counterparts, with depth locations that are consistent at least at the reference point 17). In this case, a stereoscopic depth location of the camera image, at least at the reference point 17, is fixed at the stereoscopic depth location of the reference point 17. Likewise, a stereoscopic depth location of the overlay image is related to the fixed stereoscopic depth location of the reference point 17 (e.g., fixed or adjusted as a function thereof). The virtual 3D models of the overlay image are therefore shifted in the common system of coordinates, such that the reference point 17 in the overlay image has the same depth location (e.g., the same vergence or parallax), as in the camera image. Since the stereoscopic depth location of the reference point 17 is therefore used as, for example, a reference for combining the camera image and the overlay image, the stereoscopic depth locations at other points or in other regions may be inconsistent or may not necessarily correspond to respective real ratios. This is nonetheless acceptable here, since the reference point may ultimately be the only reliably specified contact point or overlap between content or objects represented in the camera image and content or objects therein, which are not visible (e.g., concealed by the tissue wall 14).

If required, a shift is also effected in a sideways direction running perpendicular to the stereoscopic depth direction, such that the reference point 17 in the overlay image also has the same 2D coordinates as in the camera image, or as the reference point 17 depicted in the camera image, in the common 3D system of coordinates.

In a method act S9, the stereoscopic representation (e.g., a composite stereo image) is generated by the data processing device 6 from the camera image and the overlay image correspondingly (e.g., with reference to the registration and virtual positioning performed in the method act S8). If the 2D to 3D conversion was omitted in the method act S6, the 2D camera image, for example, may therefore be represented with the same stereoscopic depth location over an entire area in the stereoscopic representation, where 2D or 3D structures of the overlay image are represented as overlaid on the 2D camera image.

Figure 4:
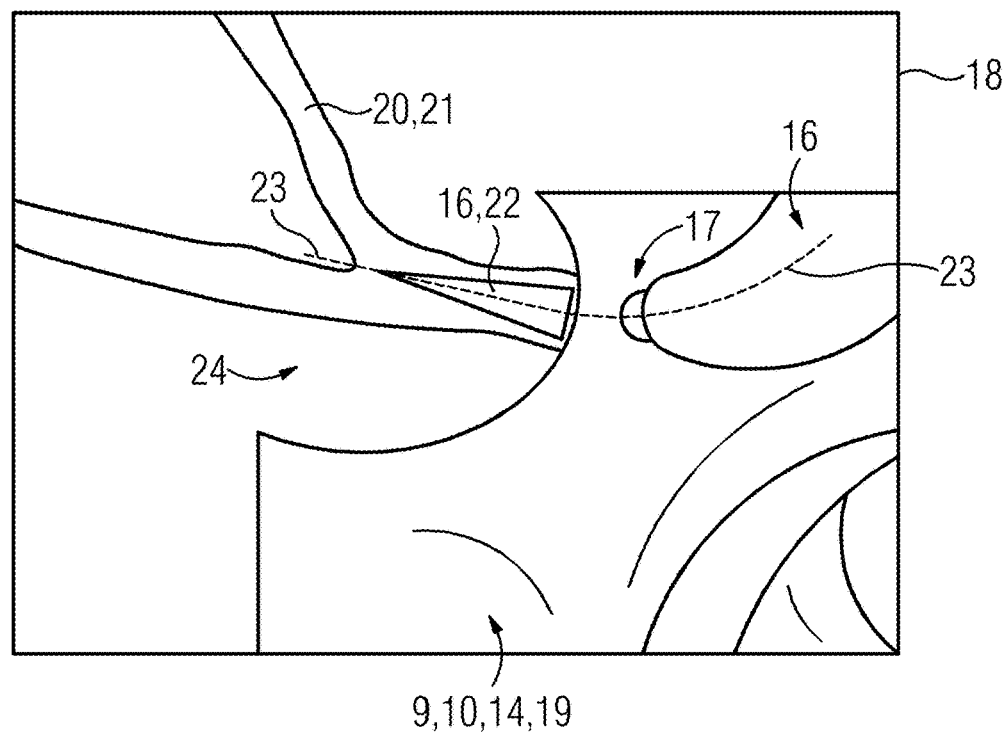
FIG. 4 shows a second schematic overview representation to illustrate the method.

FIG. 4 schematically shows a stereoscopic part-image 18 (e.g., one of two 2D views used to generate the composite stereo image). Here, an endoscope image 19 recorded by the endoscope 15 is represented as the camera image in a partial region of the stereoscopic part-image 18. A superimposition 20 is represented as the overlay image. The superimposition 20 includes, for example, a model structure 21 representing the concealed structure 11, an instrument model 22 representing a part of the instrument 16 that is situated out of sight of the endoscope 15 behind the tissue wall 14, and a travel path 23 of the instrument 16 or for the instrument 16. In this case, the travel path 23 extends in a depth direction in the stereoscopic representation, both in front of and behind the tissue wall 14. The model structure 21 and the instrument model 22 are represented in a virtual window and extend beyond an image region of the endoscope image 19.

For this purpose, the endoscope image 19 is masked in an overlap region 24 between the superimposition 20 or the model structure 21 and the instrument model 22 on one side and the endoscope image 19 on the other side. The optical view of the endoscope 15 generally offers a very small field of view. The instrument 16 and anatomical structures of interest such as, for example, the concealed structure 11 and accordingly, for example, the model structure 21, may therefore be situated at least partially outside this field of view or recording field. The field of view for the stereoscopic part-image 18 and consequently for the stereoscopic representation is therefore expanded such that all relevant structures are visible. The optical endoscope image 19 is represented in 2D and 3D correspondingly in only a section or partial region of the stereoscopic part-image 18 and also of the stereoscopic representation accordingly. Since the stereoscopic depth location of the endoscope image 19 is fixed at the fixed stereoscopic depth location of the reference point 17, the endoscope image 19, for example, at least if the optional 2D to 3D conversion was omitted in the method act S6, therefore remains in a 2D plane of the stereoscopic representation with fixed vergence, while the superimposition 20 is stereoscopically represented and extends or may extend over an elongated depth region (e.g., different vergences or vergence values).

In a method act S10, the data processing device 6 outputs the composite stereo image that has been generated (e.g., the stereoscopic representation) to the display device 5 for representation.

In all, the foregoing examples show how an improved depiction of a target object that is at least partially optically opaque may be achieved. In this case, anatomical structures, devices, planning paths, and/or similar that are situated behind the opaque region are superimposed in a corresponding camera image. Although the camera image offers only monoscopic imaging in this case, it is provided that a meaningful depth relationship that is, for example, realistic or corresponds to reality, between the camera image and the superimpositions or overlays, is nonetheless present in the resulting composite stereo image or the resulting stereoscopic representation. A specified point to which, or to the stereoscopic depth location of which, all other superimpositions or parts of the stereoscopic representation are related, is used as a depth reference in this case. A suitable representation, composed of a camera view or endoscope view and a virtual overlay, may therefore be generated based on the alignment point or reference point 17.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An imaging system for generating a stereoscopic representation of a target object, the imaging system comprising:
    an acquisition device; and
    a data processor,
    wherein the acquisition device is configured to:
        acquire an optical camera image of an optically opaque part of the target object; and
        acquire, by a material-penetrating acquisition modality, a structure that is optically concealed by the opaque part in a recording direction of the optical camera image, and
    wherein the data processor is configured to:
        automatically specify a common reference point that is depicted in the optical camera image and by the material-penetrating acquisition modality;
        automatically fix a stereoscopic depth location of the reference point at a predetermined value;
        automatically generate an overlay image based on the acquired concealed structure; and
        automatically generate the stereoscopic representation from the optical camera image and the overlay image, automatically fix a stereoscopic depth location of the optical camera image at the stereoscopic depth location of the reference point, and as a function thereof, adjust a stereoscopic depth location of the overlay image in relation to the stereoscopic depth location of the reference point, such that in the stereoscopic representation, the overlay image, at least at the reference point, appears in front of, behind, or in front of and behind the optically opaque part in the recording direction of the optical camera image in accordance with a corresponding real location in front of, behind, or in front of and behind the optically opaque part.

2. A method for generating a stereoscopic representation of a target object using an imaging system, the method comprising:
    acquiring an optical camera image of an optically opaque part of the target object;
    acquiring, by a material-penetrating acquisition modality, a structure that is optically concealed by the opaque part in a recording direction of the optical camera image;
    automatically specifying a common reference point that is depicted in the optical camera image and by the material-penetrating acquisition modality;
    automatically fixing a stereoscopic depth location of the reference point at a predetermined value;
    automatically generating an overlay image based on the acquired optically concealed structure; and
    automatically generating the stereoscopic representation from the optical camera image and the overlay image,
    wherein a stereoscopic depth location of the optical camera image is automatically fixed at the stereoscopic depth location of the reference point and, as a function thereof, a stereoscopic depth location of the overlay image is adjusted in relation to the stereoscopic depth location of the reference point, such that in the stereoscopic representation, the overlay image, at least at the reference point, appears in front of, behind, or in front of and behind the optically opaque part in the recording direction of the optical camera image in accordance with a corresponding real location in front of, behind, or in front of and behind the optically opaque part.

3. The method of claim 2, wherein a penetration point of an instrument through the optically opaque part is specified as the reference point.

4. The method of claim 2, wherein a three-dimensional (3D) model of the optically concealed structure is generated as part of the overlay image.

5. The method of claim 2, wherein a travel path for a predetermined object is generated as part of the overlay image.

6. The method of claim 2, wherein a two-dimensional (2D) position of the reference point is specified in an image plane of the optical camera image that is perpendicular to the recording direction of the camera image, and
    wherein the 2D position of the reference point is also used for 2D registration of the overlay image with the camera image in the image plane.

7. The method of claim 2, wherein a marker that is detectable optically by the material-penetrating acquisition modality is used to indicate the reference point.

8. The method of claim 2, wherein a part of the acquisition device that is used for recording the optical camera image is acquired by the material-penetrating acquisition modality, and wherein a location and direction of the part of the acquisition device in relation to the reference point is specified from corresponding acquisition data.

9. The method of claim 2, further comprising automatically adapting, in the stereoscopic representation, the optical camera image in a region in which the optical camera image overlaps the overlay image, the automatically adapting comprising masking, dimming, blurring, partially transparent representing, or any combination thereof.

10. The method of claim 2, wherein the optical camera image is recorded as a two-dimensional (2D) image, and
wherein a stereoscopic depth location of the optical camera image is fixed at the stereoscopic depth location of the reference point in the stereoscopic representation, such that the optical camera image is represented entirely and in an integrated manner at this stereoscopic depth location.

11. The method of claim 2, wherein the optical camera image is recorded as a two-dimensional (2D) image and is converted by a 2D to three-dimensional (3D) conversion method before the stereoscopic representation is generated,
wherein the stereoscopic representation is generated from the converted camera image and the overlay image,
wherein for the purpose of fixing the stereoscopic depth location of the converted camera image, a partial region of the converted camera image containing the reference point is fixed at the stereoscopic depth location of the reference point.

12. The method of claim 11, wherein a 3D recording of the optically opaque part is recorded first, and a 3D model that is generated from the 3D recording of the optically opaque part is registered with the 2D optical camera image and is used as a basis for the conversion of the 2D camera image.

13. In a non-transitory computer-readable storage medium that stores instructions executable by one or more processors to generate a stereoscopic representation of a target object using an imaging system, the instructions comprising:
acquiring an optical camera image of an optically opaque part of the target object;
acquiring, by a material-penetrating acquisition modality, a structure that is optically concealed by the opaque part in a recording direction of the optical camera image;
automatically specifying a common reference point that is depicted in the optical camera image and by the material-penetrating acquisition modality;
automatically fixing a stereoscopic depth location of the reference point at a predetermined value;
automatically generating an overlay image based on the acquired optically concealed structure; and
automatically generating the stereoscopic representation from the optical camera image and the overlay image,
wherein a stereoscopic depth location of the optical camera image is automatically fixed at the stereoscopic depth location of the reference point and, as a function thereof, a stereoscopic depth location of the overlay image is adjusted in relation to the stereoscopic depth location of the reference point, such that in the stereoscopic representation, the overlay image, at least at the reference point, appears in front of, behind, or in front of and behind the optically opaque part in the recording direction of the optical camera image in accordance with a corresponding real location in front of, behind, or in front of and behind the optically opaque part.

14. The non-transitory computer-readable storage medium of claim 13, wherein a penetration point of an instrument through the optically opaque part is specified as the reference point.

15. The non-transitory computer-readable storage medium of claim 13, wherein a three-dimensional (3D) model of the optically concealed structure is generated as part of the overlay image.

16. The non-transitory computer-readable storage medium of claim 13, wherein a travel path for a predetermined object is generated as part of the overlay image.

17. The non-transitory computer-readable storage medium of claim 13, wherein a two-dimensional (2D) position of the reference point is specified in an image plane of the optical camera image that is perpendicular to the recording direction of the camera image, and
wherein the 2D position of the reference point is also used for 2D registration of the overlay image with the camera image in the image plane.

* * * * *